US00RE47581E

(19) United States
(12) Reissued Patent
Moreno Vallejo et al.

(10) Patent Number: US RE47,581 E
(45) Date of Reissued Patent: Aug. 27, 2019

(54) MOBILE X-RAY DEVICE WITH TELESCOPIC COLUMN

(71) Applicant: SOCIEDAD ESPAÑOLA DE ELECTROMEDICINA Y CALIDAD, S.A., Algete, Madrid (ES)

(72) Inventors: Ildefonso Moreno Vallejo, Madrid (ES); Diego Sanz Parreño, Madrid (ES); Angel Garcia Alonso, Madrid (ES); Javier Fernández Juarez, Madrid (ES); Andres Causapé Rodriguez, Madrid (ES)

(73) Assignee: SOCIEDAD ESPANOLA DE ELECTROMEDICINA Y CALIDAD, S.A., Algete, Madrid (ES)

(21) Appl. No.: 15/833,939

(22) Filed: Jan. 3, 2018

Related U.S. Patent Documents

Reissue of:
(64) Patent No.: 9,521,984
Issued: Dec. 20, 2016
Appl. No.: 14/401,168
PCT Filed: Jul. 4, 2013
PCT No.: PCT/ES2013/070473
§ 371 (c)(1),
(2) Date: Nov. 14, 2014
PCT Pub. No.: WO2015/001144
PCT Pub. Date: Jan. 8, 2015

(51) Int. Cl.
*A61B 6/00* (2006.01)
*A61B 6/10* (2006.01)

(52) U.S. Cl.
CPC ..... *A61B 6/4452* (2013.01); *A61B 6/10* (2013.01); *A61B 6/4405* (2013.01); *A61B 6/447* (2013.01)

(58) Field of Classification Search
None
See application file for complete search history.

(56) References Cited

U.S. PATENT DOCUMENTS 5,544,217 A * 8/1996 Kadowaki ..... A61B 6/4405 378/193
6,193,415 B1 2/2001 Kadowaki et al. .. A61B 6/4405 378/197

(Continued)

FOREIGN PATENT DOCUMENTS

WO WO2015001144 8/2015

OTHER PUBLICATIONS

International Preliminary Report on Patentability for International Application No. PCT/ES2013/070473 dated Jan. 5, 2016.

(Continued)

*Primary Examiner* — Glenn K Dawson
(74) *Attorney, Agent, or Firm* — Neal, Gerber & Eisenberg LLP; Bradley Rademaker; Nawshaba Siddiquee

(57) ABSTRACT

Device comprising: a chassis (1) which supports the entire assembly, a telescopic column (2) which comprises a lower fixed portion (5) rotating with respect to a vertical axis, and at least one upper mobile portion (6), a telescopic arm (3) that moves along the vertical column and that supports an x-ray emitter (4) at its end, wherein the telescopic arm-head assembly can be moved from the lower position of the mobile column in its retracted position to the upper position of the mobile column in its extended position, and also in that all the movements of the column are manual and have a mechanical balancing mechanism which comprises a first mechanism consisting of a spring, a block and tackle, and a variable radius pulley all housed in the fixed portion of the column, and a second balancing mechanism consisting of a recovery pulley and a two-radii pulley which balances the weight between the input of the cable and that of the telescopic arm and head assembly.

33 Claims, 8 Drawing Sheets

(56) References Cited

U.S. PATENT DOCUMENTS

| | | | | |
|---|---|---|---|---|
| 6,302,581 | B1 * | 10/2001 | Sliski | A61N 5/1001 212/901 |
| 7,540,660 | B2 * | 6/2009 | Koyanagi | A61B 6/105 378/189 |
| 8,568,028 | B2 * | 10/2013 | Wendlandt | A61B 6/447 378/193 |
| 8,672,543 | B2 * | 3/2014 | Kralles | A61B 6/4405 378/102 |
| 8,876,379 | B2 * | 11/2014 | DiRisio | A61B 6/447 378/193 |
| 2011/0249804 | A1 * | 10/2011 | Wendlandt | A61B 6/4405 378/198 |
| 2011/0249805 | A1 | 10/2011 | Kralles et al. | |
| 2011/0249807 | A1 * | 10/2011 | Dirisio | A61B 6/447 378/198 |
| 2012/0045037 | A1 | 2/2012 | Carmichael et al. | |
| 2012/0093294 | A1 | 4/2012 | Lalena et al. | |
| 2012/0219121 | A1 * | 8/2012 | Simmons | A61B 6/4405 378/198 |
| 2012/0224673 | A1 * | 9/2012 | Barker | A61B 6/4405 378/198 |
| 2013/0129048 | A1 | 5/2013 | Chicchetti et al. | |
| 2013/0223598 | A1 * | 8/2013 | Simmons | A61B 6/4405 378/198 |
| 2014/0098943 | A1 * | 4/2014 | Omura | A61B 6/4452 378/198 |
| 2014/0133627 | A1 * | 5/2014 | Sakuragi | A61B 6/4429 378/62 |

OTHER PUBLICATIONS

International Search report/Written Opinion for International Application No. PCT/ES2013/070473 dated Mar. 26, 2014.

* cited by examiner

MOBILE X-RAY DEVICE WITH TELESCOPIC COLUMN

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

*CROSS REFERENCE TO RELATED APPLICATIONS*

*This application is a broadening Reissue of U.S. Pat. No. 9,521,984, filed on Jul. 4, 2013, and issued on Dec. 20, 2016, the entirety of which is incorporated by reference herein.*

OBJECT OF THE INVENTION

The object of the present invention, as the heading of the invention establishes, is an x-ray device with telescopic column, used to make x-rays that can reach any point in space, in any angle and/or direction, also having a design capable of adopting a configuration that facilitates moving the equipment.

The mobile x-ray device comprises a chassis that supports the entire assembly, a telescopic column that comprises a fixed portion jointed to the chassis, the fixed portion having at least one telescopic portion, the device also comprising a telescopic arm that moves along at least one telescopic portion and that supports an x-ray emitter at its end.

The present invention is characterised by the special configuration and design of each and every one of the elements forming part of the equipment, and particularly by the fact that both the column and the arm that supports the x-ray emitter are extendable telescopically, allowing any point in space to be reached, in addition to adopting a compact configuration that facilitates movement and having a balancing mechanism of all movements, of the telescopic arm along the mobile portion and of the telescopic column's extension and retraction.

Therefore, the present invention relates to the field of mobile devices for making x-rays.

BACKGROUND OF THE INVENTION

The state of the art is familiar with mobile devices for making x-rays, such as the one disclosed in patent document US 20110249807, having a chassis on which a telescopic column is disposed and associated to a telescopic arm that has an x-ray emitter at its end.

The device has means for mechanically balancing the vertical movements that take place, the movement of extension and retraction of the mobile portion of the column and the movement of the telescopic arm along the mobile portion of the column.

The means used in balancing the two movements are counterweights and/or motorised brake systems, which are costly and complex means, depend on having a power supply, and require continuous maintenance.

Consequently, the object of the present invention is to develop a mobile x-ray device that has a telescopic column and a telescopic arm that has an x-ray emitter assembled on its end, wherein the balancing means of the vertical movements are simplified, thereby developing a mobile x-ray device such as the one described herein whose essence is reflected in claim one.

DESCRIPTION OF THE INVENTION

The object of the present invention is a mobile x-ray device with a telescopic column on which there is a telescopic arm assembled that has an x-ray emitter assembled at its end, the mobile device having on the telescopic column means for balancing the vertical movement of the assembly.

The mobile x-ray device is made up of the following parts:

- An arm-head assembly made up of a telescopic arm and an x-ray emitter at its end.
- A telescopic column with a fixed lower portion and a mobile upper portion that allows positioning of the height of the arm-head assembly. This column can, in turn, rotate around a vertical axis allowing the arm-head assembly to rotate around the column on the horizontal plane.
- A telescopic arm that moves along the vertical column and that supports an X-ray emitter at its end. This arm when extending or retracting allows the x-ray emitter to be moved further away or brought closer horizontally.
- A chassis that supports the entire telescopic column and in which the manual or motorised system for moving the equipment is included, including the wheels that allow the mobile x-ray equipment to be moved.
- A head or head assembly which includes an x-ray emitter.
- A user console.

Thanks to the combination of the extendable characteristics of the telescopic column and the telescopic arm, the achievement is on the one hand to reach any part in space where an x-ray is to be made, while on the other hand, adopting a compact configuration, in such a way that during movement, the telescopic column itself does not represent an obstacle in the field of vision ahead of the mobile device.

Both the chassis and the telescopic arm incorporate a parking lock so that the emitter is locked during transport for increased safety.

This configuration for transport provides a field of vision free of obstacles for the operator driving the equipment.

The arm-head assembly can be moved from the lower position of the mobile column in its retracted position (minimum height position) to the upper position of the mobile column in its extended position (maximum height position).

In addition, all the movements of the column are manual and are mechanically balanced, making it possible to position the arm-head assembly at any height between the maximum and minimum height positions.

The movements of the elements assembled on the chassis of the mobile x-ray device include:

- Rotation of the telescopic column on the vertical axis over the horizontal plane.
- Vertical movement: extension and retraction of the telescopic column.
- Movement of the arm-head assembly over the mobile portion of the telescopic column.
- Extension and retraction of the telescopic arm
- Rotations of the head assembly.

Of all these movements there are two that are made in a vertical direction and that need to be balanced: that of the arm-head assembly over the mobile portion of the column and that of extension and retraction of the telescopic column.

In the state of the art this problem is usually resolved by means of counterweights and/or motorised brake systems. In the present invention, thanks to all the movements described above being manual and mechanically balanced correct and continuous functioning of the balancing system is ensured, in contrast to balancing systems based on electrical means, which require maintenance and have a higher risk of failure.

The mechanical balancing mechanism provided to the invention is divided into two parts:

- a first mechanism that balances the weight of the assembly of the two bodies with vertical movement. These two bodies are the mobile part of the column and the arm-head assembly. This mechanism consists of the fixed column, the block and tackle, the spring, and the variable-radius pulley).
- a second mechanism that balances the weight of the arm-head assembly. This second mechanism consists of the mobile column, the recovery pulley and the two-radii pulley.

The second balancing mechanism can be modified to admit further vertical telescopic portions by merely adding one new variable radius pulley and one new recovery pulley for each new portion of telescopic column.

The compact telescopic arm comprises various portions, a base portion joined to the column and at least one other portion which slides horizontally with respect to the base portion.

EXPLANATION OF THE DRAWINGS

To complement the description being made and with a view to contributing towards a better understanding of the characteristics of the invention, according to a preferred example of a practical embodiment thereof, a set of drawings is attached as an integral part of said description, which by way of illustration and not limitation, represent the following.

FIG. 3 shows the minimum height position. FIG. 4 shows the maximum height position.

PREFERRED EMBODIMENT OF THE INVENTION

In the light of the drawings what follows is a description of a preferred mode of embodiment of the proposed invention.

Figure 1:
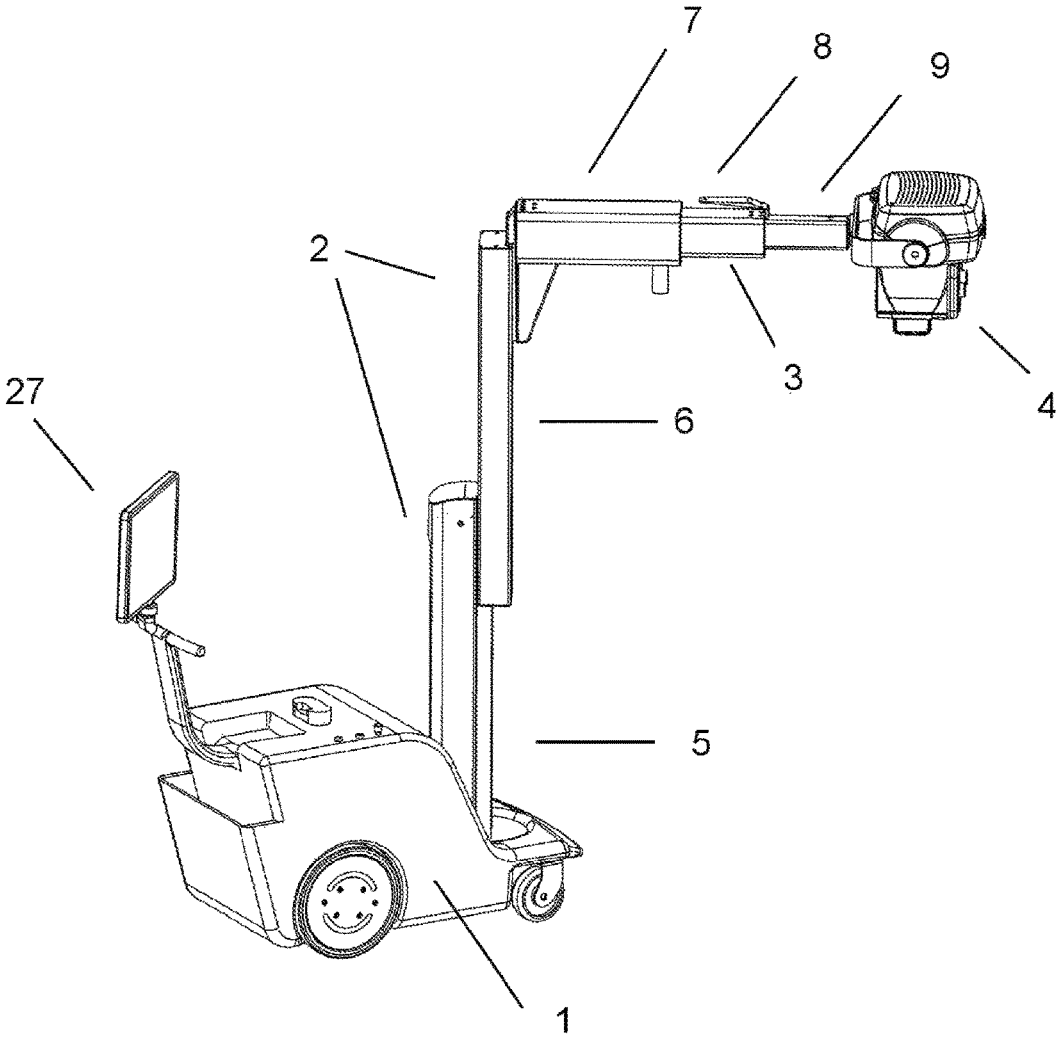
In FIG. 1, it is possible to observe a general representation of the mobile x-ray device comprising the object of the invention.

In FIG. 1 it is possible to observe that the mobile device that is the object of the invention comprises:

- A chassis (1) that supports the telescopic column and having a system with wheels for manual or motorised movement which allow the equipment to be transported.
- A telescopic column (2) comprising a lower portion fixed in height (5) which rotates with respect to the vertical axis, and at least one portion mobile in height (6).
- A telescopic arm (3) which moves vertically along the telescopic column and which supports at its end a head assembly (4) where the x-ray emitter is located. This arm when extending or retracting allows the x-ray emitter to be moved further away or brought closer horizontally.

The head assembly (4) includes the x-ray emitter.

The telescopic arm (3) comprises a base portion (7) and at least one other horizontally mobile portion. In a possible mode of embodiment, said telescopic arm comprises:

- A base portion (7) fixed to the telescopic column (2) by means of a joint that is moveable along the last portion (the highest) of the telescopic column.
- Two portions (8) and (9) which slide horizontally with respect to the base portion (7).

Figure 2:
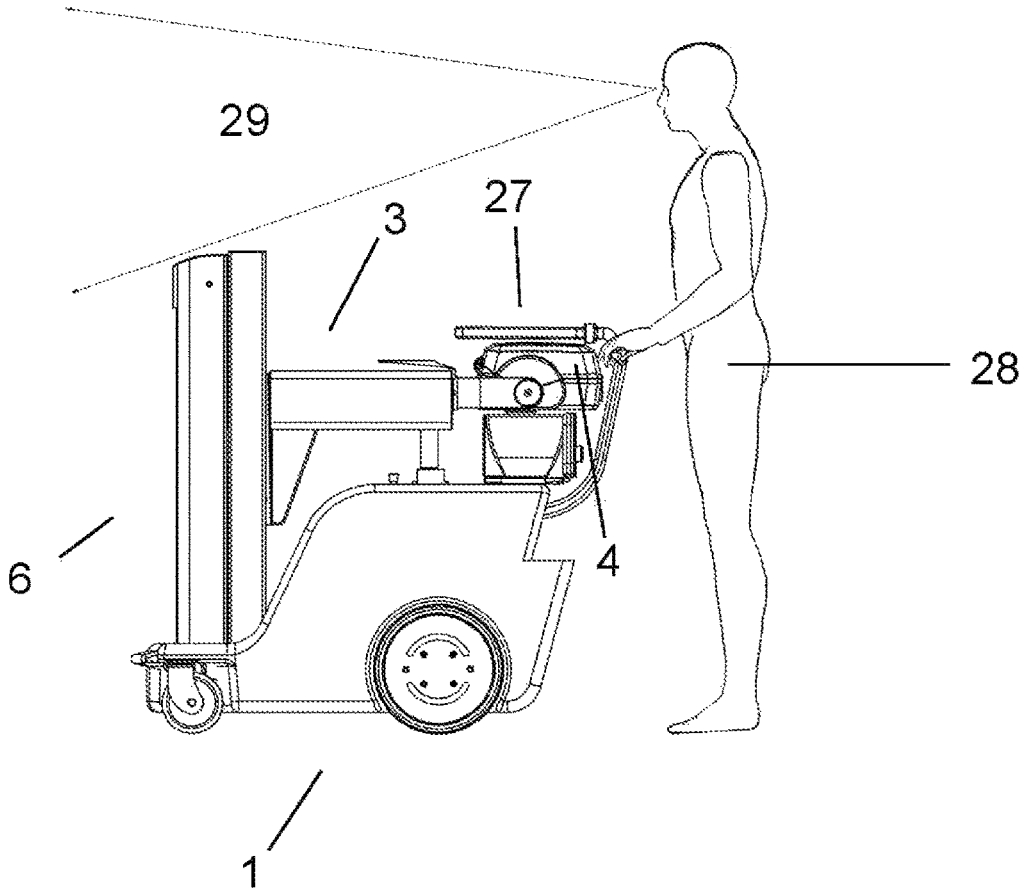
FIG. 2 shows a representation of the device in the compact and retracted position.

In FIG. 2, it is possible to observe the retracted (parking) position of both, the telescopic column (2) and the telescopic arm (3), a convenient position for transport of the mobile device, and how a user (28) has an unrestricted field of vision (29).

Figure 10:
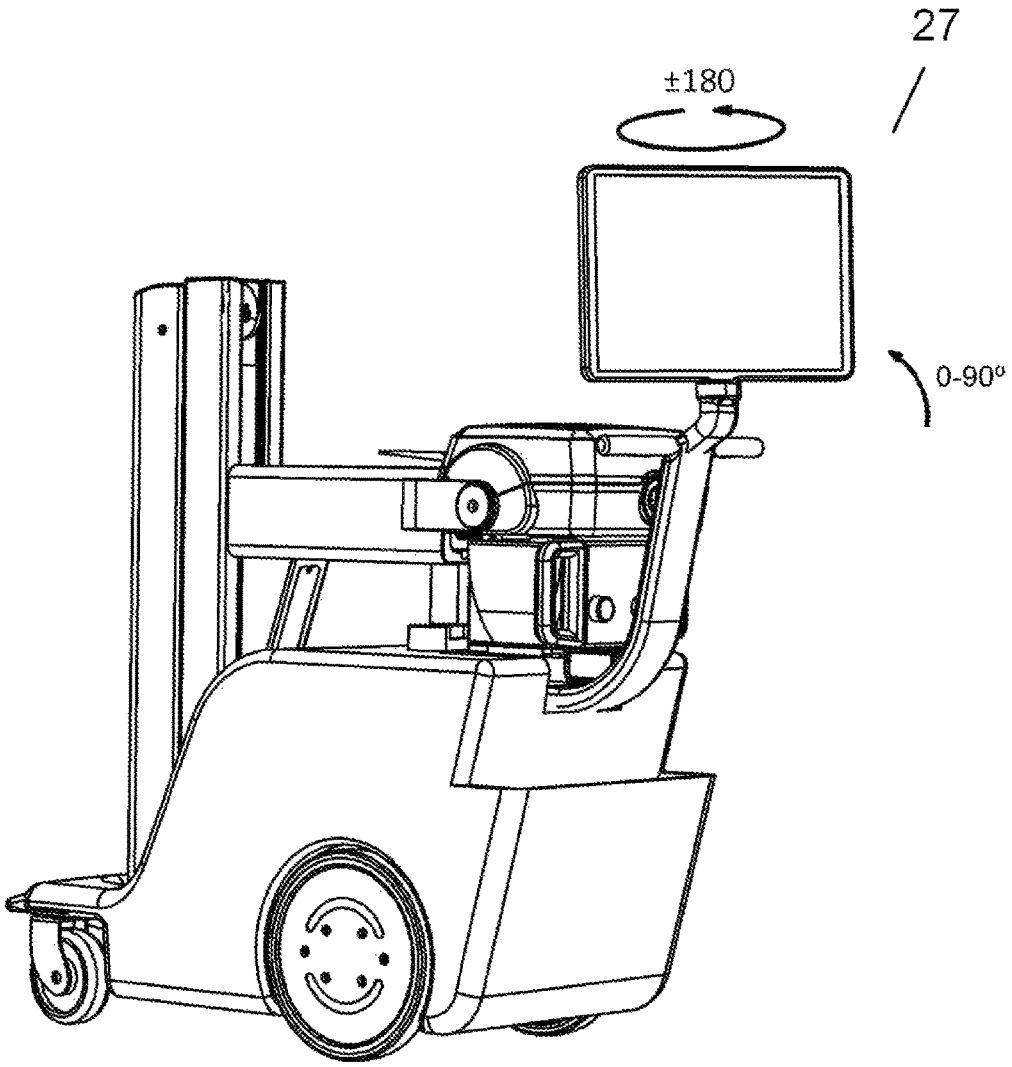
FIG. 10 shows a representation of the device in the compact and retracted position showing the different possibilities of rotation of the user console.

FIGS. 1, 2 and 10 show the presence of a user console (27). In FIG. 1, the user console (27) is unfolded, whereas in FIG. 2, the user console (27) is folded.

In FIG. 10, the user console (27) can rotate between 0° and 90° on the horizontal axis and additionally shows how the user console (27) could rotate between −180° and +180° on the vertical axis.

Figure 3:
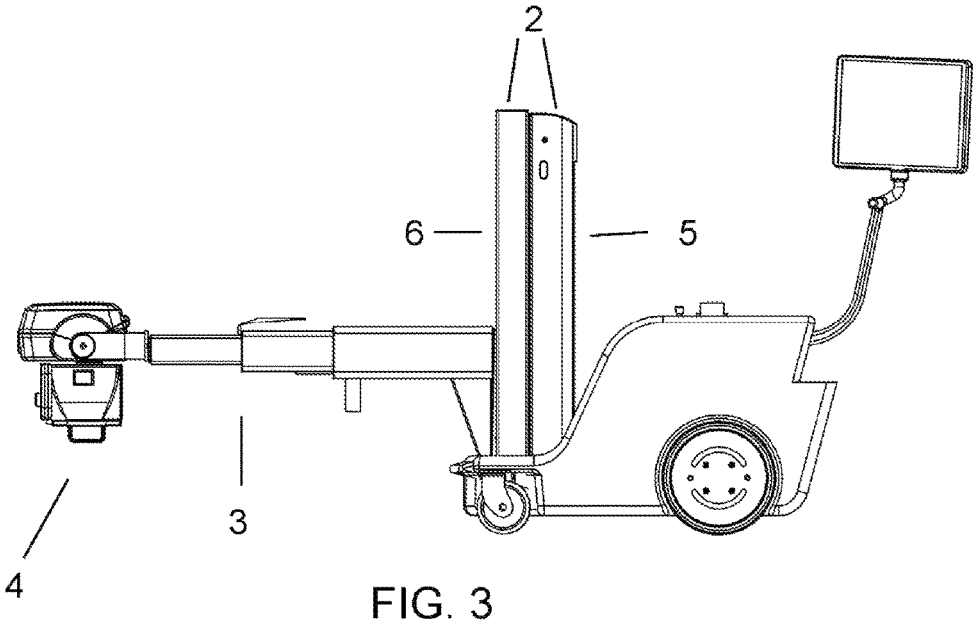
FIGS. 3 and 4 show the extreme positions that the arm-head assembly can adopt in terms of height.
Figure 4:
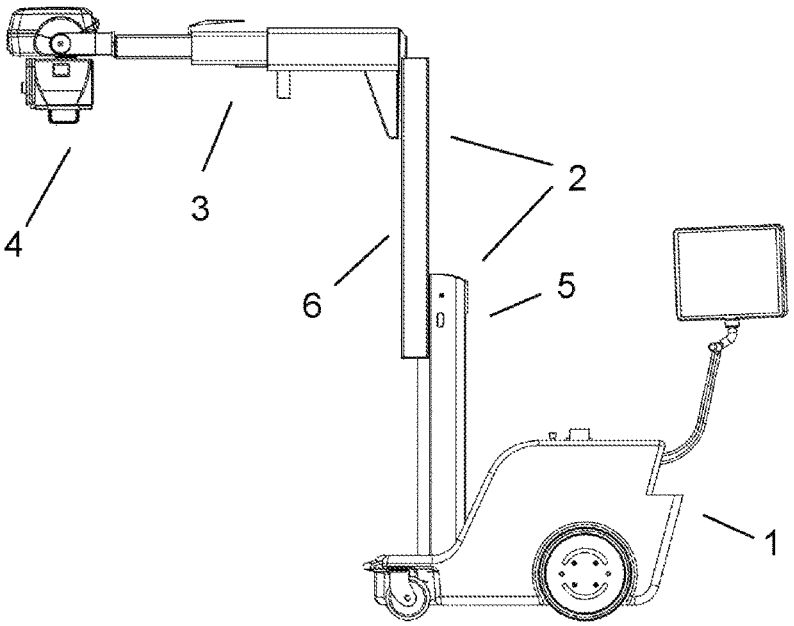

FIGS. 3 and 4 show the extreme positions in height that the assembly consisting of the telescopic arm (3) and the head assembly (4) can adopt, which range from the lowest position of the mobile portion (6) of the telescopic column (2) in the retracted position (FIG. 3), to the highest position of the mobile portion (6) of the telescopic column (2) in the extended position (FIG. 4).

Figure 5:
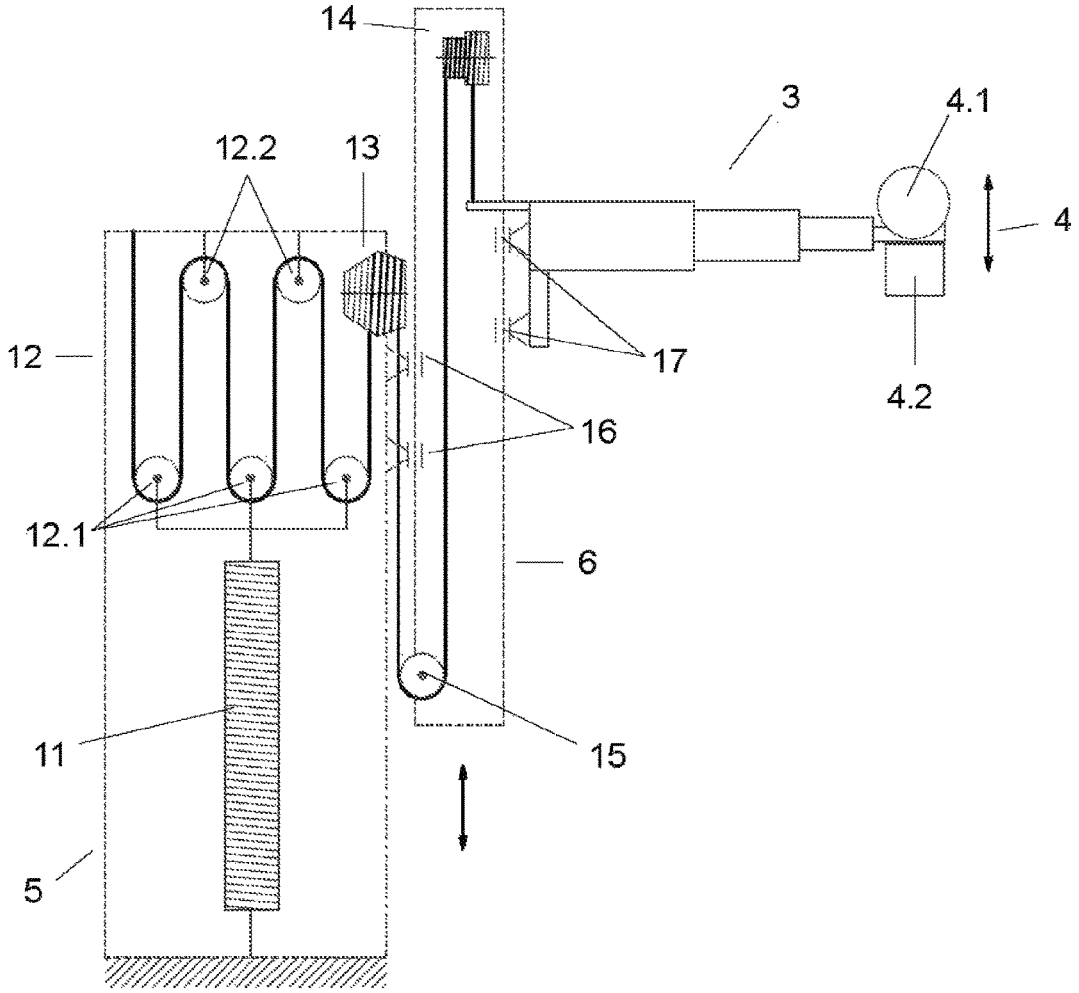
FIG. 5 shows the mechanical balancing means of the telescopic column in a simplified manner.

FIG. 5 shows schematically in detail the mechanical balancing mechanism which comprises:

- A first mechanism which balances the weight of the suspended bodies that move vertically (the mobile portion (6) of the telescopic column (2) on the one hand, and the telescopic arm (3) with the head assembly (4) on the other hand). This first mechanism is housed in the fixed lower portion (5) of the telescopic column (2).
- A second mechanism which balances the weight of the assembly consisting of the telescopic arm (3) and the head assembly (4) and which is housed in each of the mobile portions (6) that the telescopic column (2) comprises.

The first balancing mechanism comprises:

- A tension spring (11) using any type of traction technology, which is the device in charge of storing the potential gravitational energy of the mobile suspended bodies in the form of potential elastic energy when these move downwards and which would return it when these bodies move upwards.
- A block and tackle (12) in charge of dividing the force of the spring (11) and multiplying the run of the cable at the output. The degree of multiplication and division depends on the number of pulleys of the block and tackle (12). In the represented case, the multiplication factor is 6. The block and tackle (12) consists of one group of lower pulleys (12.1) and one group of upper pulleys (12.2).

A variable radius pulley (13). The cable that comes from the block and tackle that is joined to the spring (11) coils in the grooves of a pulley wherein the radii vary throughout the run of the cable, achieving the cable at the output of said variable radius pulley having a constant tension. This force will be the sum of the weights to be balanced (that of the mobile portion (6) of the telescopic column (2) and that of the telescopic arm (3) and head assembly (4).

The fixed column houses the elements mentioned above: the spring (11), the block and tackle (12) and the variable radius pulley (13).

The fixed portion (5) of the telescopic column (2) is fixed to the frame of the chassis and can rotate on it. The rotation mechanism incorporates an orifice concentric with the column that allows passage of the system's electrical cables that run from the chassis (1) to the telescopic column (2) and whose final destination is any device between said orifice and up to the head assembly (4).

In a possible mode of embodiment of the block and tackle (12), it is possible to achieve with only two axes the coaxial alignment of the upper pulleys (12.2) and the variable radius pulley (13) on the one hand with the lower pulleys (12.1) on the other, although this does not exclude other possible block and tackle configurations that can perform the same function.

The system represented in FIG. 5 has two degrees of freedom in a vertical direction wherein the movement is manual and balanced. Therefore, if the head assembly (4) is moved manually in a vertical direction there is uncertainty in respect of which of the two vertical guides will start to move. Due to different friction of the vertical guides (16) and (17) only one of the two will move until it reaches a stopper, and as of that moment the other one will start to move.

The second balancing mechanism comprises:

A two-radii pulley (14) that takes charge of balancing the weight of the telescopic arm (3) and of the head assembly (4) with the traction at the input of this pulley (sum of the mobile portion (6) of the telescopic column (2) plus the telescopic arm (3) and head (4) assembly). This is achieved by making the ratio between the input and output radii equal to the weight of the arm-head assembly divided by the weight of the mobile portion (6) plus the telescopic arm (3) and head assembly (4), in other words, the ratio between input radius and output radius is equal to the quotient between weight [(3)+(4)] divided by weight [(6)+(3)+(4)]. This two-radii pulley (14) is fixed to the upper part of the mobile portion (6) of the telescopic column (2).

A recovery pulley (15) that allows the cable that comes from the variable radius pulley (13) to pull upwards from the lower part of the mobile portion (6) of the telescopic column (2).

This second balancing mechanism is housed in the mobile portion (6), therefore housing the recovery pulley (15), and the two-radii pulley (14). Furthermore, it has the linear guides (16) between the mobile portion (6) and the fixed portion (5), and the linear guides (17) between the mobile portion (6) and the telescopic arm (3).

The second balancing mechanism can be modified to admit further portions, as many as the mobile portions of the telescopic column (2), by merely adding a new two-radii pulley and a recovery pulley for each new portion of mobile column.

In this FIG. 5, the telescopic arm (3) has also been represented, which at its end has the head assembly (4) consisting of the x-ray emitter (4.1) and the x-ray collimator (4.2).

Figure 6:
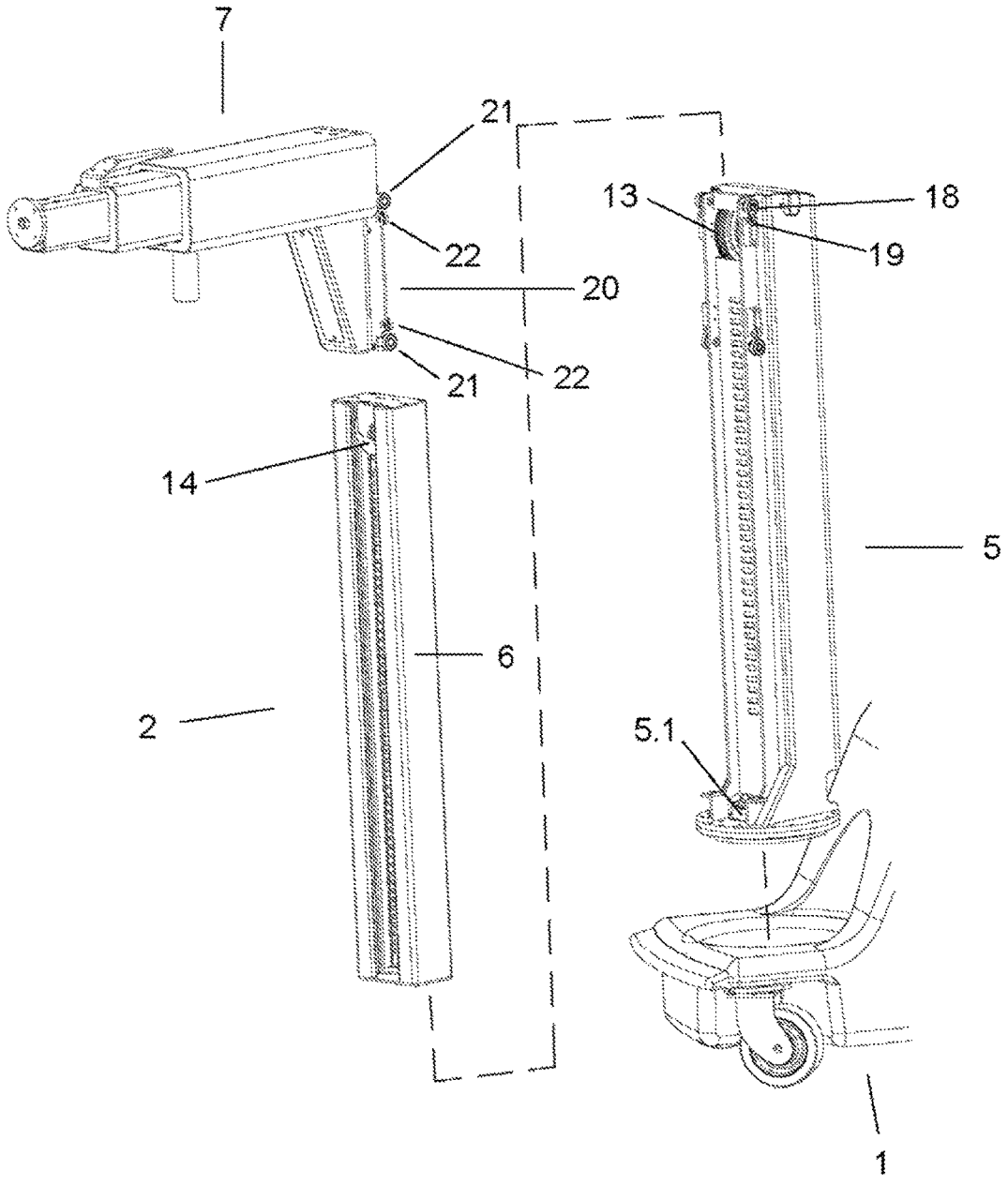
FIG. 6 shows an exploded view of the telescopic column and the mechanical balancing means housed inside.

In FIG. 6, it is possible to observe the elements previously described, with the rotary joint between the lower fixed portion (5) and the chassis (1) being particularly noteworthy, which is achieved by means of a ball bearing (5.1), said joint having a concentric orifice through which the system's electrical cables are made to pass which run from the chassis (1) to the fixed portion (5) and whose final destination can be any device between said orifice and the head assembly (4) including its components.

On the fixed portion (5) of the telescopic column (2) front bearings (18) and lateral bearings (19) are disposed on either side, which allow the movement of the mobile portion (6) with respect to the fixed portion (5), without heaving or pitching.

A base plate (20) can also be observed for the movement of the telescopic arm (3) wherein the base portion (7) is shown. Said base plate (20) has at both its upper end and its lower end and on both sides front bearings (21) and other lateral bearings (22) which allow perfect guiding without heaving or pitching of the telescopic arm (3) in its vertical movement along the mobile portion (6) to which it is associated.

Figure 7:
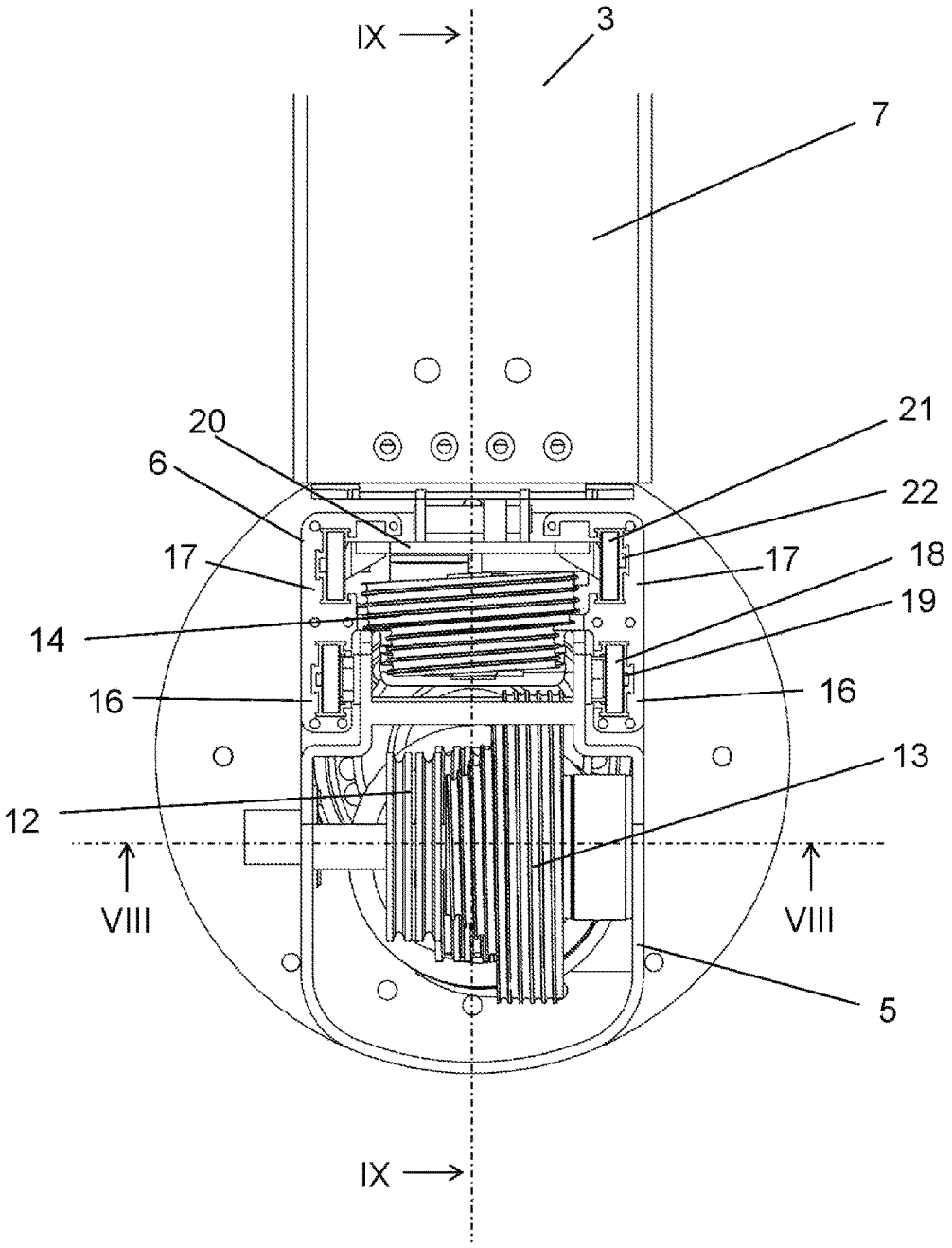
FIG. 7 shows a top view representation of the telescopic column.

In FIG. 7, the guides (16) between the fixed portion (5) and the mobile portion (6) and the guides (17) between the telescopic arm (3) and the mobile portion (6) can be observed. Guides (16) house the front bearings (18) and lateral bearings (19). Guides (17) house the front bearings (21) and lateral bearings (22).

Figures 8, 9:
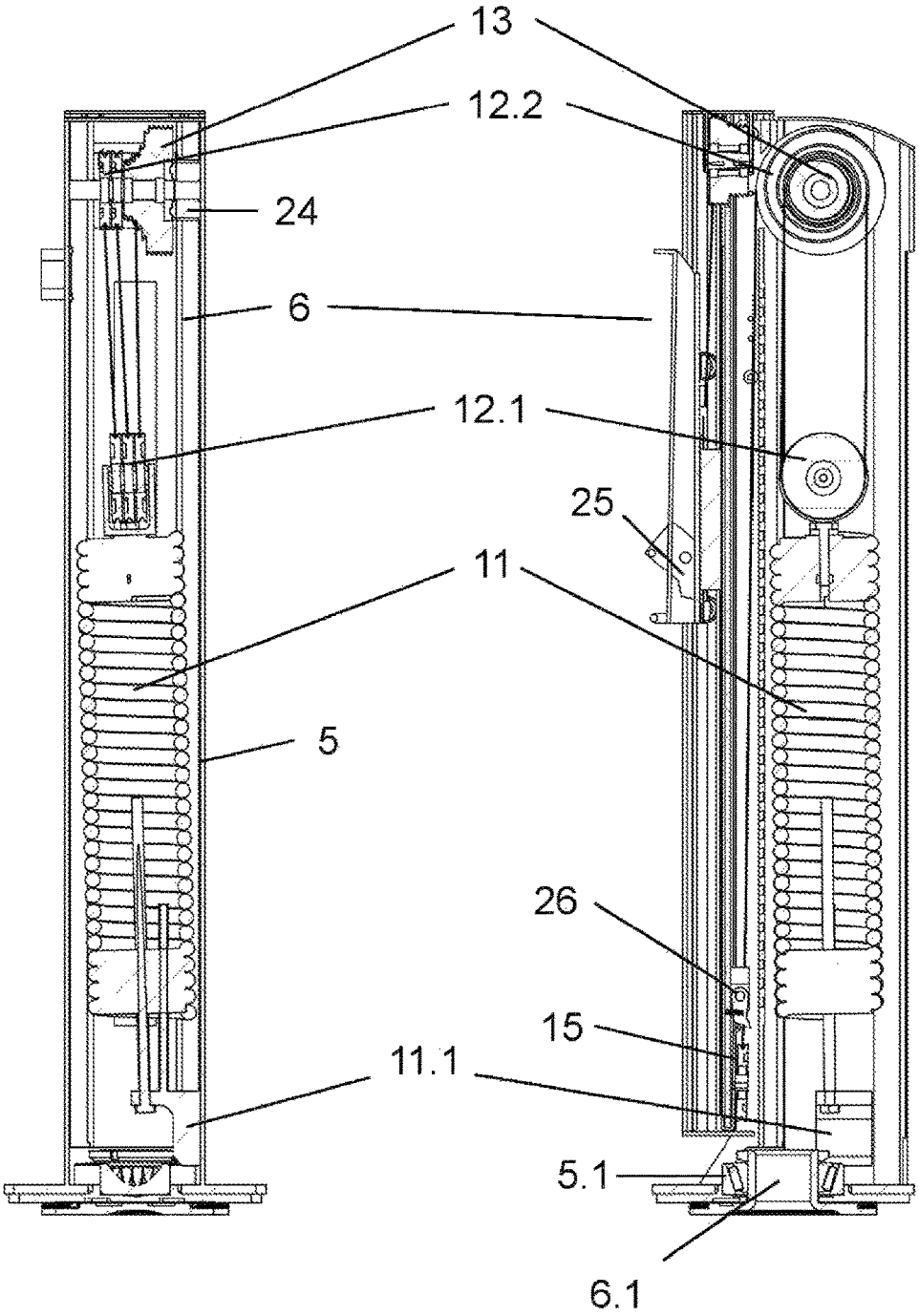
FIGS. 8 and 9 show two sections made of the telescopic column on the planes VIII-VIII and IX-IX respectively. These section planes are indicated in FIG. 7.

FIGS. 8 and 9 show sections of the telescopic column, wherein the support (11.1) of the spring (11) at its lower end can be observed.

Also the mechanical balancing mechanism has safety means, which in a possible mode of embodiment comprise:

An electromagnetic brake (24) mounted on the variable radius pulley (13)

A first parachute mechanism (25) which prevents the assembly consisting of the telescopic arm (3) and the head assembly (4) from falling in the event of the cable breaking A second parachute mechanism (26) which prevents the mobile portion (6) from falling in the event of the cable breaking.

Having sufficiently described the nature of the present invention, in addition to a way of putting it into practice, it is stated that, within its essence, it may be put into practice in other modes of embodiment which differ in detail to the one portrayed by way of an example, and to which the protection sought hereby will likewise extend, on condition that its fundamental principle is not altered, changed or modified.

The invention claimed is:

1. A mobile x-ray device comprising:

a chassis;

a telescopic column comprising a lower fixed portion connected to the chassis and rotatable relative to the chassis with respect to a first vertical axis, and at least one upper mobile portion being vertically moveable relative to the lower fixed portion, *wherein said lower fixed portion is fixed in height*;

a telescopic arm connected to the upper mobile portion of the telescopic column and supporting at its end a head assembly which contains an x-ray emitter, the telescopic arm being horizontally extendable and retractable relative to the telescopic column, thus allowing the x-ray emitter to be moved further away or brought closer horizontally to the telescopic column;

the telescopic arm further being vertically moveable relative to the upper mobile portion of the telescopic column;

a cable connected to the upper mobile portion and the telescopic arm for providing the vertical movement of the mobile portion and telescopic arm in response to movement of the cable;

a first mechanism housed within the fixed portion for balancing the weight of the mobile portion and the telescopic arm during the vertical movement thereof, the first mechanism including a block and tackle connected to the cable for multiplying the run of the cable, and a tension spring connected to and extending between the chassis and the block and tackle for storing potential gravitational energy of the upper mobile portion and telescopic arm in the form of elastic energy when the upper mobile portion moves downwardly and returns the stored energy when the mobile portion move upwardly, and a variable radius pulley receiving the cable; and a second mechanism housed within the upper mobile portion for balancing the weight of the telescopic arm and the head assembly, the second mechanism including at least one two-radii pulley and a recovery pulley, each connected to the cable.

2. A mobile x-ray device according to claim 1, further including a plurality of wheels with manual or motorized movement connected to the chassis for allowing the mobile x-ray device to be moved.

3. A mobile x-ray device according to claim 1, wherein the telescopic arm comprises:

a base portion connected to the mobile portion of the telescopic column by means of a joint moveable along the mobile portion; and two sliding portions which slide horizontally with respect to the base portion and with respect to one another.

4. A mobile x-ray device according to claim 1, wherein the block and tackle consists of one group of lower pulleys and one group of upper pulleys, wherein the lower pulleys of the block and tackle are joined to the tension spring;

the variable radius pulley defines a plurality of grooves with varying radii, and wherein the cable extends from the block and tackle and is coiled in the grooves of the *variable radius* pulley, thereby achieving that the cable at [the] *an* output of the *variable radius* pulley has a constant tension, and wherein [the] *a* force applied to the cable at the output of the *variable radius* pulley is the sum of the weight of the mobile portion and that of the telescopic arm with the head assembly.

5. A mobile x-ray device according to claim 1, wherein the two-radii pulley includes an input portion having an input radius and an output portion having an output radius, and wherein the two-radii pulley achieves a balancing of forces by making the ratio between the input radius divided by the output radius equal to the sum of the weights of the telescopic arm assembly and the weight of the head assembly divided by the sum of the weights of the mobile portion, the telescopic arm assembly and the head assembly.

6. A mobile x-ray device according to claim 1, wherein linear guides are positioned between the mobile portion and the fixed portion, and linear guides are positioned between the mobile portion and the telescopic arm.

7. A mobile x-ray device with telescopic column according to claim 1, wherein a rotary joint interconnects the lower fixed portion and the chassis and provides [the] *a* rotary movement of the lower fixed portion relative to the chassis, wherein the rotary joint includes a bearing and defines an orifice, and wherein a plurality of electrical cables pass from the chassis to the inside of the fixed portion through the orifice.

8. A mobile x-ray device according to claim 1, wherein the fixed portion of the telescopic column includes first front bearings and lateral bearings disposed between the fixed portion and the mobile portion which allow movement of the mobile portion with respect to the fixed portion without heaving or pitching; and the telescopic arm includes a base plate that has an upper end and a lower end, and wherein second front bearings and side bearings are connected to the upper and lower ends of the base plate and disposed between the base plate and the mobile portion for guiding the telescopic arm in its vertical movement over the mobile portion to which it is associated.

9. A mobile x-ray device according to claim 4, further including a first parachute mechanism disposed between the telescopic arm and the mobile portion, and a second parachute disposed between the mobile portion and the fixed portion, wherein the parachute mechanisms prevent the possible fall of the telescopic arm of the head assembly and of the mobile portion in the event of the cable breaking.

10. A mobile x-ray device according to claim 4, wherein a rotary [join] *joint* interconnects the lower fixed portion and the chassis and provides [the] *a* rotary movement of the lower fixed portion relative to the chassis, and wherein the rotary joint includes a rotation bearing and defines an orifice concentric with respect to the rotation bearing which allows passage of electrical cables from the chassis to the telescopic column.

11. A mobile x-ray device according to claim 1, [wherein the assembly comprises] *further comprising* a user console.

12. A mobile x-ray device according to claim 11, wherein the user console rotates between 0° and 90° about a horizontal axis which is generally perpendicular to the first vertical axis.

13. A mobile x-ray device with telescopic column according to claim 12, wherein the user console rotates between −180° and +180° about a second vertical axis being parallel to the first vertical axis.

*14. An x-ray device, comprising:*

*a chassis;*

*a telescopic column comprising a lower portion connected to the chassis and an upper portion vertically moveable relative to the lower portion;*

*a telescopic arm connected to the upper portion of the telescopic column and including an x-ray assembly, the telescopic arm being vertically moveable relative to the upper portion of the telescopic column and horizontally extendable and retractable relative to the telescopic column;*

*a single cable connected to the telescopic column and to the telescopic arm;*

*said cable being connected to a first mechanism housed within the lower portion, the first mechanism including a pulley assembly for multiplying the run of the cable, a tension spring connected to and extending between a*

*support within the lower portion of the column and the pulley assembly, and a variable radius pulley to counterbalance a weight of the upper portion and the telescopic arm during vertical movement of each; and*

*said cable being further connected to a second mechanism located between the first mechanism and the telescopic arm, wherein said second mechanism includes a dual-radius pulley and a recovery pulley.*

*15. The x-ray device of claim 14, wherein the pulley assembly is configured to provide the cable to an input of the variable radius pulley.*

*16. The x-ray device of claim 15, wherein the pulley assembly is a block and tackle comprising a group of lower pulleys and a group of upper pulleys, and wherein the cable extends from the group of upper pulleys to the variable radius pulley.*

*17. The x-ray device of claim 16, wherein the tension spring is connected between the group of lower pulleys and the support within the lower portion of the telescopic column.*

*18. The x-ray device of claim 14, wherein the second mechanism is positioned within the upper portion of the telescopic column.*

*19. The x-ray device of claim 14, wherein the variable radius pulley defines a plurality of grooves with varying radii, the cable being coiled in the grooves to achieve a constant tension in the cable at an output of the variable radius pulley.*

*20. The x-ray device of claim 14, wherein the recovery pulley connects the cable at the output of the variable radius pulley to an input of the dual-radius pulley.*

*21. An x-ray device, comprising:*

*a telescopic column comprising a lower portion and an upper portion vertically moveable along an extent of the lower portion;*

*a telescopic arm coupled to the upper portion and supporting an x-ray assembly, the telescopic arm being vertically moveable along the upper portion and horizontally extendable and retractable relative to the telescopic column;*

*a cable movably connected to the telescopic column and the telescopic arm, movement of the cable causing the vertical movement of the upper portion and the vertical movement of the telescopic arm;*

*a first balancing mechanism housed within the lower portion and including a first pulley assembly connected to the cable for multiplying the run of the cable, a variable radius pulley receiving the cable from an output of the first pulley assembly, and a tension spring coupled between the first pulley assembly and a support within the lower portion of the column, the tension spring storing potential gravitational energy of the upper portion and the telescopic arm in the form of elastic energy when the upper portion moves downwardly and returning the stored elastic energy when the upper portion moves upwardly; and*

*a second balancing mechanism located between the first balancing mechanism and the telescopic arm and including a multi-radii pulley and a recovery pulley, each connected to the cable received from the first balancing mechanism.*

*22. The x-ray device of claim 21, wherein the first pulley assembly comprises a group of upper pulleys and a group of lower pulleys, the cable extending from the group of upper pulleys to an input of the variable radius pulley, and the tension spring being coupled to the group of lower pulleys.*

*23. The x-ray device of claim 21, wherein the variable radius pulley defines a plurality of grooves with varying radii, the cable being coiled in the grooves to achieve a constant tension in the cable at an output of the variable radius pulley.*

*24. The x-ray device of claim 21, wherein the multi-radii pulley assembly includes a multi-radii pulley and a recovery pulley, the multi-radii pulley including an input portion with an input radius and an output portion with an output radius different from the input radius.*

*25. The x-ray device of claim 21, wherein the telescopic arm comprises:*

*a base portion connected to the upper portion of the telescopic column by means of a joint moveable along the upper portion; and*

*two sliding portions which slide horizontally with respect to the base portion and with respect to one another.*

*26. The x-ray device of claim 21, wherein the second balancing mechanism is positioned within the upper portion of the telescopic column to balance the weight of the telescopic arm and the x-ray assembly.*

*27. A mobile x-ray assembly, comprising:*

*an x-ray machine and a wheeled chassis for moving the assembly and a telescopic support assembly, the telescopic support assembly comprising a vertically extending telescopic column and a horizontally extending telescopic arm supporting an x-ray emitter head assembly, wherein:*

*said telescopic column is rotatable about a vertical axis and comprising a lower portion and an upper portion, said upper portion being vertically moveable along an extent of the lower portion;*

*said telescopic arm having a first end moveably coupled to said upper portion and a second end supporting the x-ray emitter head assembly, wherein said telescopic arm is extendable and retractable to adjustably extend and retract the position of the head assembly relative to the telescoping column; and*

*an elongated cable member extending between the lower portion of the column and the telescopic arm, said cable member being connected to a first mechanism located at the lower portion of the telescopic column for storing potential energy when the upper portion is moved toward the lower portion and wherein said first mechanism includes a pulley assembly for multiplying the run of the cable, a tension spring connected to and extending between the pulley assembly and a support in the lower portion of the column, and a variable radius pulley;*

*said cable member further being connected to a second mechanism positioned between the first mechanism and said telescopic arm, said second mechanism including a multi-radius pulley and a recovery pulley.*

*28. The mobile x-ray assembly of claim 27, wherein the pulley assembly is a block and tackle positioned between the tension spring and the variable radius pulley.*

*29. The mobile x-ray assembly of claim 28, wherein the block and tackle comprises a group of lower pulleys and a group of upper pulleys, said lower pulleys of the block and tackle connected to the tension spring.*

*30. The mobile x-ray assembly of claim 29, wherein the cable member extends from the block and tackle, is coiled about the variable radius pulley, and extends to said second mechanism.*

*31. The mobile x-ray assembly of claim 30, wherein said cable member is engaged with said recovery pulley and said*

*multi-radius pulley, and wherein an end of said cable member is connected to said telescopic arm.*

*32. The mobile x-ray assembly of claim 27, wherein the telescopic arm comprises:*

*a base portion connected to the upper portion of the telescopic column by means of a joint moveable along the upper portion; and*

*two sliding portions which slide horizontally with respect to the base portion and with respect to one another.*

*33. The mobile x-ray assembly of claim 27, wherein the second mechanism is positioned within the upper portion of the telescopic column to balance the weight of the telescopic arm and the x-ray emitter head assembly.*

* * * * *